US008974429B2

(12) United States Patent
Gordon et al.

(10) Patent No.: US 8,974,429 B2
(45) Date of Patent: Mar. 10, 2015

(54) APPARATUS AND METHOD FOR APPLYING TOPICAL NEGATIVE PRESSURE

(75) Inventors: Benjamin Gordon, Cambridge (GB); Jake Turner, Cambridgeshire (GB); Nathan Wrench, Cambridgeshire (GB); Edward Vernon-Harcourt, Pulborough (GB); David Harris, Cambridge (GB)

(73) Assignee: Smith & Nephew PLC, London (GB)

( * ) Notice: Subject to any disclaimer, the term of this patent is extended or adjusted under 35 U.S.C. 154(b) by 252 days.

(21) Appl. No.: 12/672,055

(22) PCT Filed: Jun. 27, 2008

(86) PCT No.: PCT/GB2008/050511
§ 371 (c)(1),
(2), (4) Date: Feb. 3, 2010

(87) PCT Pub. No.: WO2009/019495
PCT Pub. Date: Feb. 12, 2009

(65) Prior Publication Data
US 2011/0071483 A1 Mar. 24, 2011

(30) Foreign Application Priority Data

Aug. 6, 2007 (GB) .................................. 0715211.9

(51) Int. Cl.
*A61M 25/00* (2006.01)
*A61M 27/00* (2006.01)
(Continued)

(52) U.S. Cl.
CPC ............ *A61M 1/0031* (2013.01); *A61M 1/0088* (2013.01); *A61M 27/00* (2013.01);
(Continued)

(58) Field of Classification Search
USPC .................................. 604/317–319, 355, 543
See application file for complete search history.

(56) References Cited

U.S. PATENT DOCUMENTS

| 5,356,378 A | 10/1994 | Doan |
| 5,690,831 A | 11/1997 | Kenley et al. |

(Continued)

FOREIGN PATENT DOCUMENTS

| GB | 2418738 | 4/2006 |
| WO | WO 03/092620 | 11/2003 |

(Continued)

OTHER PUBLICATIONS

U.S. Appl. No. 12/667,229, filed Dec. 29, 2009, published as 2010/0207768, including its ongoing prosecution history, including without limitation Office Actions, Amendments, Remarks, and any other potentially relevant documents.

(Continued)

*Primary Examiner* — Tatyana Zalukaeva
*Assistant Examiner* — Sara Sass
(74) *Attorney, Agent, or Firm* — Knobbe, Martens, Olson & Bear, LLP

(57) ABSTRACT

A method and apparatus for alerting a user of topical negative pressure therapy apparatus to a full waste canister condition are described, the apparatus comprising a device having vacuum pump means and a waste canister connected to the device and the waste canister operably connected to a wound dressing by aspiration conduit means for aspirating fluid from the wound, the aspiration conduit means, the waste canister and the device providing a fluid flow path therethrough and the vacuum pump means providing fluid flow through the apparatus, the apparatus further comprising fluid flow restriction means in the fluid flow path of said vacuum pump and fluid pressure sensing means upstream and downstream of said fluid flow restriction means.

14 Claims, 10 Drawing Sheets

(51) Int. Cl.
*G01F 1/36* (2006.01)
*A61M 1/00* (2006.01)

(52) U.S. Cl.
CPC ........ *A61M 1/0025* (2013.01); *A61M 2205/18* (2013.01); *A61M 2205/3331* (2013.01); *A61M 2205/3382* (2013.01); *A61M 2205/8206* (2013.01)
USPC ............................ 604/319; 604/318; 604/320

(56) References Cited

U.S. PATENT DOCUMENTS

| | | | |
|---|---|---|---|
| 5,744,027 A | | 4/1998 | Connell et al. |
| 5,951,863 A | | 9/1999 | Kruger et al. |
| 6,387,086 B2 | | 5/2002 | Mathias et al. |
| 6,503,219 B2 | | 1/2003 | Milsom |
| 6,558,340 B1 | | 5/2003 | Traeger |
| 6,585,675 B1 | | 7/2003 | O'Mahony et al. |
| 6,602,468 B2 | | 8/2003 | Patterson et al. |
| 6,620,379 B1 * | | 9/2003 | Piuk et al. ........................ 422/3 |
| 6,691,047 B1 | | 2/2004 | Fredricks |
| 6,868,739 B1 * | | 3/2005 | Krivitski et al. ........... 73/861.05 |
| 6,916,424 B2 | | 7/2005 | Collins et al. |
| 7,004,923 B2 | | 2/2006 | Deniega et al. |
| 7,278,981 B2 | | 10/2007 | Ellingboe et al. |
| 7,438,705 B2 | | 10/2008 | Karpowicz et al. |
| 7,553,306 B1 | | 6/2009 | Hunt et al. |
| 7,615,158 B2 | | 11/2009 | Sternby et al. |
| 7,666,171 B2 | | 2/2010 | Mombrinie et al. |
| 7,744,553 B2 | | 6/2010 | Kelly et al. |
| 7,776,001 B2 | | 8/2010 | Brugger et al. |
| 7,927,319 B2 | | 4/2011 | Lawhorn |
| 8,308,714 B2 | | 11/2012 | Weston et al. |
| 8,449,487 B2 | | 5/2013 | Hovland et al. |
| 8,529,487 B2 | | 9/2013 | Fava et al. |
| 8,663,200 B2 | | 3/2014 | Weston et al. |
| 2002/0156464 A1 * | | 10/2002 | Blischak et al. ........... 604/892.1 |
| 2002/0198504 A1 * | | 12/2002 | Risk et al. ................... 604/318 |
| 2003/0235635 A1 * | | 12/2003 | Fong et al. ...................... 425/73 |
| 2004/0167482 A1 * | | 8/2004 | Watson ........................ 604/317 |
| 2005/0166683 A1 * | | 8/2005 | Krivitski et al. ........... 73/861.05 |
| 2006/0025727 A1 * | | 2/2006 | Boehringer et al. ........... 604/313 |
| 2006/0059980 A1 * | | 3/2006 | Matsubara et al. ........... 73/118.1 |
| 2006/0129137 A1 * | | 6/2006 | Lockwood et al. ........... 604/543 |
| 2007/0032763 A1 | | 2/2007 | Vogel |
| 2008/0071234 A1 | | 3/2008 | Kelch et al. |
| 2008/0281281 A1 | | 11/2008 | Meyer et al. |
| 2010/0185164 A1 | | 7/2010 | Hartwell et al. |
| 2010/0207768 A1 | | 8/2010 | Pidgeon et al. |
| 2010/0211030 A1 | | 8/2010 | Turner et al. |
| 2010/0211031 A1 | | 8/2010 | Hartwell |
| 2010/0249691 A1 | | 9/2010 | Van Der Mooren et al. |
| 2010/0278518 A1 | | 11/2010 | Gordon et al. |
| 2010/0298792 A1 | | 11/2010 | Weston et al. |
| 2011/0008179 A1 | | 1/2011 | Turner et al. |
| 2011/0028921 A1 | | 2/2011 | Hartwell et al. |
| 2011/0130730 A1 | | 6/2011 | Hartwell et al. |

FOREIGN PATENT DOCUMENTS

| | | |
|---|---|---|
| WO | WO 03/101508 | 12/2003 |
| WO | WO 2006/052745 | 5/2006 |
| WO | WO 2006/135934 | 12/2006 |
| WO | WO 2007/013064 | 2/2007 |
| WO | WO 2007/062024 | 5/2007 |
| WO | WO 2008/010094 | 1/2008 |
| WO | WO 2008/030872 | 3/2008 |
| WO | WO 2008/036360 | 3/2008 |
| WO | WO 2008/039314 | 4/2008 |
| WO | WO 2008/048481 | 4/2008 |
| WO | WO 2008/049029 | 4/2008 |

OTHER PUBLICATIONS

U.S. Appl. No. 12/667,228, filed Dec. 29, 2009, published as 2010/0211030, including its ongoing prosecution history, including without limitation Office Actions, Amendments, Remarks, and any other potentially relevant documents.

U.S. Appl. No. 12/667,232, filed Dec. 29, 2009, published as 2010/0211031, including its ongoing prosecution history, including without limitation Office Actions, Amendments, Remarks, and any other potentially relevant documents.

U.S. Appl. No. 12/672,468, filed Feb. 5, 2010, including its ongoing prosecution history, including without limitation Office Actions, Amendments, Remarks, and any other potentially relevant documents, Vernon-Harcourt et al.

U.S. Appl. No. 12/672,472, filed Feb. 19, 2011, including its ongoing prosecution history, including without limitation Office Actions, Amendments, Remarks, and any other potentially relevant documents, Turner et al.

U.S. Appl. No. 12/808,547, filed Oct. 13, 2010, published as 2011/0028921, including its ongoing prosecution history, including without limitation Office Actions, Amendments, Remarks, and any other potentially relevant documents.

U.S. Appl. No. 12/672,192, filed Feb. 4, 2010, published as 2011/0130730, including its ongoing prosecution history, including without limitation Office Actions, Amendments, Remarks, and any other potentially relevant documents.

U.S. Appl. No. 12/918,2011, filed Mar. 28, 2011, including its ongoing prosecution history, including without limitation Office Actions, Amendments, Remarks, and any other potentially relevant documents, Hartwell et al.

Info V.A.C. User Manual—KCI—Dec. 2006 (76 pages).

International Search Report from PCT/GB2008/050511, mailed Oct. 31, 2008 in 4 pages.

Written Opinion from PCT/GB2008/050511, mailed Oct. 31, 2008 in 4 pages.

International Preliminary Report on Patentability Chapter I from PCT/GB2008/050511, mailed Feb. 9, 2010 in 6 pages.

U.S. Appl. No. 14/179,434, filed Feb. 12, 2014, including its ongoing prosecution history, including without limitation Office Actions, Amendments, Remarks, and any other potentially relevant documents, Weston et al.

* cited by examiner

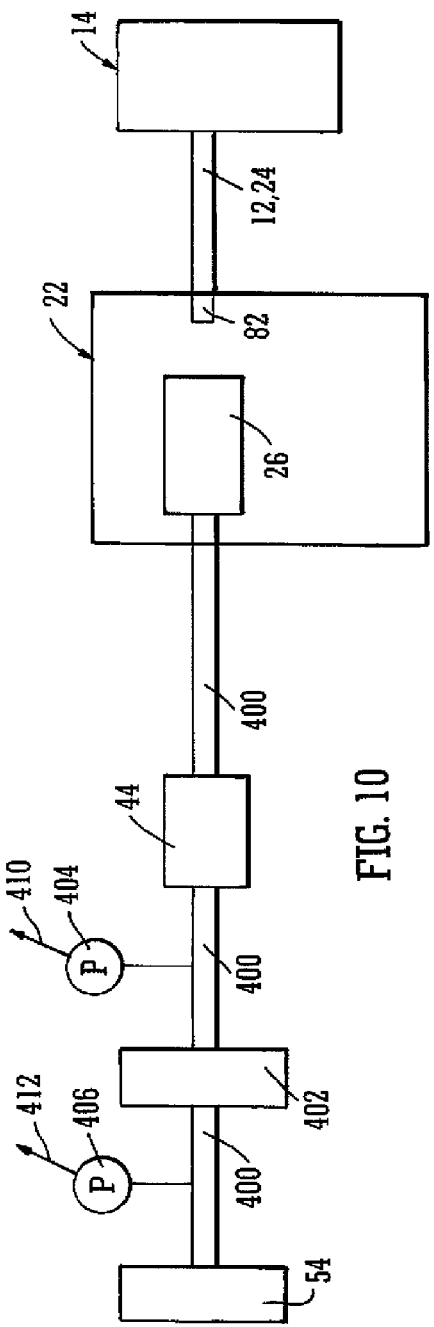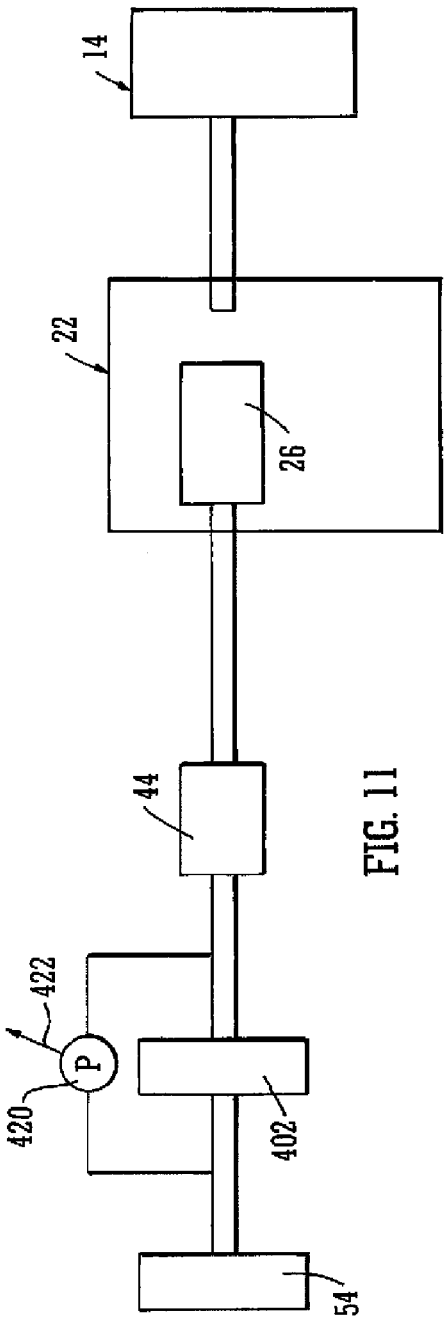

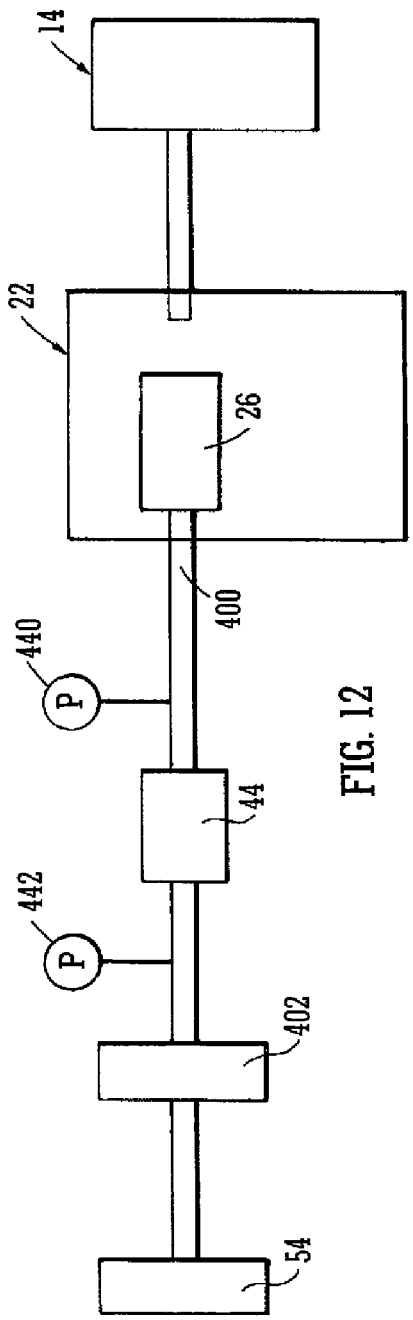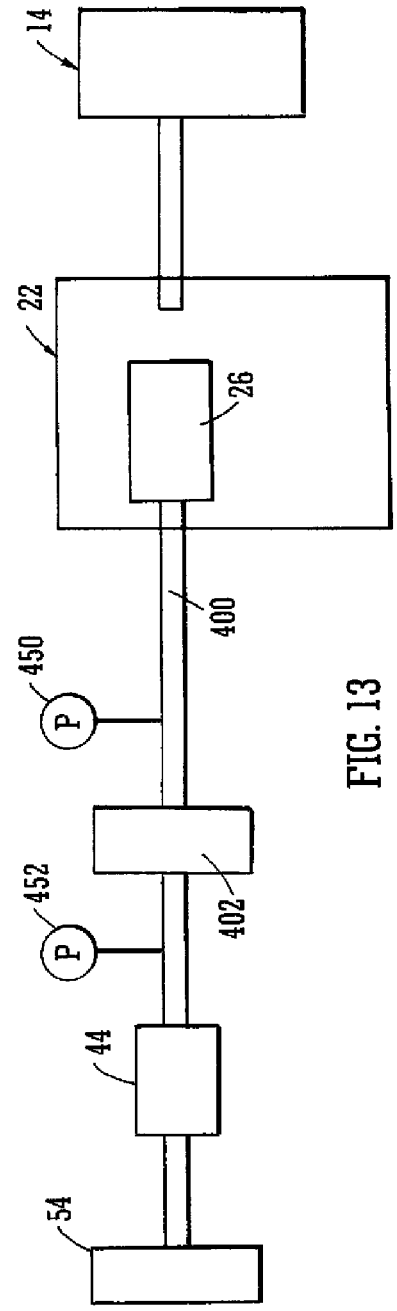

APPARATUS AND METHOD FOR APPLYING TOPICAL NEGATIVE PRESSURE

CROSS-REFERENCE TO RELATED APPLICATIONS

This Application is a U.S. National Phase of the International Application No. PCT/GB2008/050511 filed Jun. 27, 2008 designating the U.S. and published on Feb. 12, 2009 as WO 2009/019495, which claims priority of Great Britain Patent Application No. 0715211.9 filed Aug. 6, 2007.

BACKGROUND OF THE INVENTION

Field of the Invention

The present invention relates to apparatus and a method for the application of topical negative pressure (TNP) therapy to wounds. In particular, but not exclusively, the present invention relates to apparatus and a method of alerting a user of TNP apparatus of a full waste canister.

BACKGROUND OF THE INVENTION

There is much prior art available relating to the provision of apparatus and methods of use thereof for the application of TNP therapy to wounds together with other therapeutic processes intended to enhance the effects of the TNP therapy. Examples of such prior art include those listed and briefly described below.

TNP therapy assists in the closure and healing of wounds by reducing tissue oedema; encouraging blood flow and granulation of tissue; removing excess exudates and may reduce bacterial load and thus, infection to the wound. Furthermore, TNP therapy permits less outside disturbance of the wound and promotes more rapid healing.

In our co-pending International patent application, WO 2004/037334, apparatus, a wound dressing and a method for aspirating, irrigating and cleansing wounds are described. In very general terms, this invention describes the treatment of a wound by the application of topical negative pressure (TNP) therapy for aspirating the wound together with the further provision of additional fluid for irrigating and/or cleansing the wound, which fluid, comprising both wound exudates and irrigation fluid, is then drawn off by the aspiration means and circulated through means for separating the beneficial materials therein from deleterious materials. The materials which are beneficial to wound healing are recirculated through the wound dressing and those materials deleterious to wound healing are discarded to a waste collection bag or vessel.

In our co-pending International patent application, WO 2005/04670, apparatus, a wound dressing and a method for cleansing a wound using aspiration, irrigation and cleansing wounds are described. Again, in very general terms, the invention described in this document utilises similar apparatus to that in WO 2004/037334 with regard to the aspiration, irrigation and cleansing of the wound, however, it further includes the important additional step of providing heating means to control the temperature of that beneficial material being returned to the wound site/dressing so that it is at an optimum temperature, for example, to have the most efficacious therapeutic effect on the wound.

In our co-pending International patent application, WO 2005/105180, apparatus and a method for the aspiration, irrigation and/or cleansing of wounds are described. Again, in very general terms, this document describes similar apparatus to the two previously mentioned documents hereinabove but with the additional step of providing means for the supply and application of physiologically active agents to the wound site/dressing to promote wound healing.

The content of the above references is included herein by reference.

However, the above apparatus and methods are generally only applicable to a patient when hospitalised as the apparatus is complex, needing people having specialist knowledge in how to operate and maintain the apparatus, and also relatively heavy and bulky, not being adapted for easy mobility outside of a hospital environment by a patient, for example.

Some patients having relatively less severe wounds which do not require continuous hospitalisation, for example, but whom nevertheless would benefit from the prolonged application of TNP therapy, could be treated at home or at work subject to the availability of an easily portable and maintainable TNP therapy apparatus.

SUMMARY OF SOME EXEMPLIFYING EMBODIMENTS

It is an aim of embodiments of the present invention to provide a method of alerting a user of TNP therapy apparatus of a full waste canister According to a first aspect of the present invention there is provided a method of alerting a user of topical negative pressure therapy apparatus to a full waste canister condition, the apparatus comprising a device having vacuum pump means and a waste canister connected to the device and the waste canister operably connected to a wound dressing by aspiration conduit means for aspirating fluid from the wound, the aspiration conduit means, the waste canister and the device providing a fluid flow path therethrough and the vacuum pump means providing fluid flow therethrough, the method comprising the steps of placing fluid flow restriction means in the fluid flow path of said vacuum pump and monitoring fluid pressures upstream and downstream of said fluid flow restriction means.

According to a second aspect of the present invention there is provided apparatus for alerting a user of topical negative pressure therapy apparatus to a full waste canister condition, the apparatus comprising a device having vacuum pump means and a waste canister connected to the device and the waste canister operably connected to a wound dressing by aspiration conduit means for aspirating fluid from the wound, the aspiration conduit means, the waste canister and the device providing a fluid flow path therethrough and the vacuum pump means providing fluid flow through the apparatus, the apparatus further comprising fluid flow restriction means in the fluid flow path of said vacuum pump and fluid pressure sensing means upstream and downstream of said fluid flow restriction means.

For the avoidance of doubt reference to "a full canister" may also mean a "blockage" in the aspiration fluid flow path and vice versa, either condition requiring attention by a user or carer.

The invention is comprised in part of an overall apparatus for the provision of TNP therapy to a patient in almost any environment. The apparatus is lightweight, may be mains or battery powered by a rechargeable battery pack contained within a device (henceforth, the term "device" is used to connote a unit which may contain all of the control, power supply, power supply recharging, electronic indicator means and means for initiating and sustaining aspiration functions to a wound and any further necessary functions of a similar nature). When outside the home, for example, the apparatus may provide for an extended period of operation on battery power and in the home, for example, the device may be connected to the mains by a charger unit whilst still being used and operated by the patient.

The overall apparatus of which the present invention is a part comprises: a dressing covering the wound and sealing at least an open end of an aspiration conduit to a cavity formed over the wound by the dressing; an aspiration tube comprising at least one lumen therethrough leading from the wound dressing to a waste material canister for collecting and holding wound exudates/waste material prior to disposal; and, a power, control and aspiration initiating and sustaining device associated with the waste canister.

The dressing covering the wound may be any type of dressing normally employed with TNP therapy and, in very general terms, may comprise, for example, a semi-permeable, flexible, self-adhesive drape material, as is known in the dressings art, to cover the wound and seal with surrounding sound tissue to create a sealed cavity or void over the wound. There may aptly be a porous barrier and support member in the cavity between the wound bed and the covering material to enable an even vacuum distribution to be achieved over the area of the wound. The porous barrier and support member being, for example, a gauze, a foam, an inflatable bag or known wound contact type material resistant to crushing under the levels of vacuum created and which permits transfer of wound exudates across the wound area to the aspiration conduit sealed to the flexible cover drape over the wound.

The aspiration conduit may be a plain flexible tube, for example, having a single lumen therethrough and made from a plastics material compatible with raw tissue, for example. However, the aspiration conduit may have a plurality of lumens therethrough to achieve specific objectives relating to the invention. A portion of the tube sited within the sealed cavity over the wound may have a structure to enable continued aspiration and evacuation of wound exudates without becoming constricted or blocked even at the higher levels of the negative pressure range envisaged.

It is envisaged that the negative pressure range for the apparatus embodying the present invention may be between about −50 mmHg and −200 mmHg (note that these pressures are relative to normal ambient atmospheric pressure thus, −200 mmHg would be about 560 mmHg in practical terms). Aptly, the pressure range may be between about −75 mmHg and −150 mmHg. Alternatively a pressure range of up to −75 mmHg, up to −80 mmHg or over −80 mmHg can be used. Also aptly a pressure range of below −75 mmHg could be used. Alternatively a pressure range of over −100 mmHg could be used or over −150 mmHg.

The aspiration conduit at its distal end remote from the dressing may be attached to the waste canister at an inlet port or connector. The device containing the means for initiating and sustaining aspiration of the wound/dressing may be situated between the dressing and waste canister, however, in a preferred embodiment of the apparatus embodying the present invention, the device may aspirate the wound/dressing via the canister thus, the waste canister may preferably be sited between the wound/dressing and device.

The aspiration conduit at the waste material canister end may preferably be, bonded to the waste canister to prevent inadvertent detachment when being caught on an obstruction, for example.

The canister may be a plastics material moulding or a composite unit comprising a plurality of separate mouldings. The canister may aptly be translucent or transparent in order to visually determine the extent of filling with exudates. However, the canister and device may in some embodiments provide automatic warning of imminent canister full condition and may also provide means for cessation of aspiration when the canister reaches the full condition.

The canister may be provided with filters to prevent the exhaust of liquids and odours therefrom and also to prevent the expulsion of bacteria into the atmosphere. Such filters may comprise a plurality of filters in series. Examples of suitable filters may comprise hydrophobic filters of 0.2 μm pore size, for example, in respect of sealing the canister against bacteria expulsion and 1 μm against liquid expulsion.

Aptly, the filters may be sited at an upper portion of the waste canister in normal use, that is when the apparatus is being used or carried by a patient the filters are in an upper position and separated from the exudate liquid in the waste canister by gravity. Furthermore, such an orientation keeps the waste canister outlet or exhaust exit port remote from the exudate surface.

Aptly the waste canister may be filled with an absorbent gel such as ISOLYSEL (trade mark), for example, as an added safeguard against leakage of the canister when full and being changed and disposed of. Added advantages of a gel matrix within the exudate storing volume of the waste canister are that it prevents excessive movement, such as slopping, of the liquid, minimises bacterial growth and minimises odours.

The waste canister may also be provided with suitable means to prevent leakage thereof both when detached from the device unit and also when the aspiration conduit is detached from the wound site/dressing.

The canister may have suitable means to prevent emptying by a user (without tools or damage to the canister) such that a full or otherwise end-of-life canister may only be disposed of with waste fluid still contained.

The device and waste canister may have mutually complementary means for connecting a device unit to a waste canister whereby the aspiration means in the device unit automatically connects to an evacuation port on the waste canister such that there is a continuous aspiration path from the wound site/dressing to an exhaust port on the device.

Aptly, the exhaust port from the fluid path through the apparatus is provided with filter means to prevent offensive odours from being ejected into the atmosphere.

In general terms the device unit may comprise an aspirant pump; means for monitoring pressure applied by the aspirant pump; a flowmeter to monitor fluid flow through the aspirant pump; a control system which controls the aspirant pump in response to signals from sensors such as the pressure monitoring means and the flowmeter, for example, and which control system also controls a power management system with regard to an on-board battery pack and the charging thereof and lastly a user interface system whereby various functions of the device such as pressure level set point, for example, may be adjusted (including stopping and starting of the apparatus) by a user. The device unit may contain all of the above features within a single unified casing.

In the general structure of the device described in the preceding paragraph a system for determining and alerting a user to a full canister condition may be based on a flowmeter sensor. In such a system the control system monitors readings of fluid flow through a flowmeter at intervals and when the fluid (gas) flow approaches or falls to zero an alarm is activated to warn the user of the condition. In reality the fluid flow may fall to zero due either to the aspiration conduit being blocked (by wound exudate, for example) or to the waste canister being full and the exit port filters in the waste canister being blocked, for example. Thus, the flowmeter in the system effectively equates low or zero flow, when the pump is otherwise functioning normally, to a blocked or full waste system. In any event, whether the aspiration conduit is blocked or the waste canister is full it is a condition which requires attention from the user to rectify since under both circumstances the wound is not being aspirated.

In the present invention and alternatively to the flowmeter-based control system described in the preceding two paragraphs, a flowmeter is dispensed with and a flow restriction, such as a small orifice, is placed in the fluid flow path within the device exhaust system, preferably at a position near to an exhaust outlet port. Aptly the fluid flow restriction may be placed downstream of the vacuum aspirant pump. A pressure sensor monitors the pressure differential at upstream and downstream positions relative to the restriction. Alternatively, two pressure sensors may be used to monitor pressure in the fluid flow path at upstream and downstream position relative to the restriction, signals from the two pressure sensors being monitored by the control system and the difference therebetween calculated at intervals. When the pressure differential or difference between the two positions tends to zero the control system interprets this as the fluid flow also tending to zero which as in the flowmeter based system effectively equates this as a full or blocked waste system as before.

The size of the restriction placed in the fluid flow path towards the exhaust may be an aperture, aptly a round aperture as this is the most economic shape to make, but does not exclude other shapes such as square or hexagonal, for example, of a size of less than 1 mm diameter or, more preferably, lying between 0.05 to 1.0 mm in diameter. The actual size may depend upon the flow rate of fluid passing through the fluid flow path. In general typical pumps used in the present apparatus may have flow rates, open port, in the range from 4 to 20 l/min. This flow rate clearly reduces as the vacuum or negative pressure in the system up to the dressing increases. An example of a suitable pump for use in the present apparatus may have an open port flow rate of 4.8 l/min. Under free flow conditions where there is no blockage in the aspirant conduit and the waste canister is substantially less than full, flow rates of up to 3 l/min have been measured with such a pump. Thus, the size of the aperture must be chosen so as to produce accurate pressure signals at low flow rates when the aspirated system is becoming full or otherwise blocked and flow rates tend to zero on the downstream side of the pump. The size of the tubing used in the flow path on the downstream side of the pump also has an effect on flow rates. In general the tubing used in what is effectively the exhaust system of the apparatus is desirably of a suitable bore which does not itself impede flow too much and tubing sizes of 3 mm and above are preferred. In general a flow rate of about 0.1 l/min minimum may be needed in order to maintain flow of wound exudate from the wound/dressing site, through the aspiration conduit and into the waste canister, this flow rate being dependent to an extent on other factors such as the bore size of the aspiration conduit, for example.

When the fluid flow through the apparatus is relatively high and relatively unrestricted, an abnormal burden may be placed on the vacuum pump causing it to operate inefficiently or perhaps necessitating a larger or more powerful than necessary pump to overcome the flow restriction caused by the restrictor. In some embodiments to deal with this possible disadvantage, a variable area flow restrictor electrically connected to the control system may be employed. A pressure sensor upstream of the flow restrictor sends signals to the control system. When that pressure is greater than a stored value in the control system memory, the control system adjusts the area of the variable area flow restrictor so that the area is increased and the flow restriction consequently reduced. When fluid flow falls due to an impending or actual blockage in the fluid flow system, the pressure sensed by the sensor connected to the control system falls to below the stored value causing the control system to adjust the variable area flow restrictor to a lower, predetermined value. At this lower, predetermined value the flow is restricted so that accuracy of pressure sensing is enhanced at low flow rates of gaseous aspirated fluid and the control system operates as before to activate an alarm when flow rates fall to a level where the pressure differential sensed falls below a stored value in the control system.

As an alternative to a variable area flow restrictor, a by-pass conduit across a fixed aperture flow restrictor may be employed, the by-pass having a valve therein. The valve may be a settable valve adjusted to open and permit flow through the by-pass conduit when the pressure upstream of the restrictor is greater than the preset value in the settable valve. Thus, load on the pump is reduced under normal free-flow operating conditions. When the fluid flow rate starts to fall and the pressure drops below the preset value in the valve, the valve closes and fluid flow is again directed through a fixed area restrictor.

In the present invention, the control system may work with the following logic steps:
1. Initiate blockage sensing process
2. Read pressure sensor value
3. Compare value to stored minimum value
4. If read value is less than stored value the system is considered blocked (or the canister is full)
5. Trigger the "Canister full" alarm (visual and/or audible)
6. End blockage sensing process
7. Repeat when next required (based on software timings).

Aptly, the control system may trigger alarm means such as a flashing light, buzzer or any other suitable means when various abnormal conditions apply such as, for example: pressure outside set value by a large amount due to a gross leak of air into system; duty on the aspiration pump too high due to a relatively smaller leakage of air into the system; pressure differential between wound site and pump is too high due, for example, to a blockage or waste canister full as is relevant to the present invention.

In view of the fact that the device unit contains the majority of the intrinsic equipment cost therein ideally it will also be able to survive impact, tolerate cleaning in order to be reusable by other patients.

In terms of pressure capability the aspiration means may be able to apply a maximum pressure drop of at least −200 mmHg to a wound site/dressing. The apparatus is capable of maintaining a predetermined negative pressure even under conditions where there is a small leak of air into the system and a high exudate flow.

The pressure control system may prevent the minimum pressure achieved from exceeding for example −200 mmHg so as not to cause undue patient discomfort. The pressure required may be set by the user at a number of discreet levels such as −50, −75, −100, −125, −150, −175 mmHg, for example, depending upon the needs of the wound in question and the advice of a clinician. Thus suitable pressure ranges in use may be from −25 to −80 mmHg, or −50 to −76 mmHg, or −50 to −75 mmHg as examples. The control system may also advantageously be able to maintain the set pressure within a tolerance band of +/−10 mmHg of the set point for 95% of the time the apparatus is operating given that leakage and exudation rates are within expected or normal levels.

The apparatus of the present invention may be provided with a carry case and suitable support means such as a shoulder strap or harness, for example. The carry case may be adapted to conform to the shape of the apparatus comprised in the joined together device and waste canister. In particular, the carry case may be provided with a bottom opening flap to permit the waste canister to be changed without complete removal of the apparatus form the carry case.

The carry case may be provided with an aperture covered by a displaceable flap to enable user access to a keypad for varying the therapy applied by the apparatus.

BRIEF DESCRIPTION OF THE DRAWINGS

In order that the present invention may be more fully understood, examples will now be described by way of illustration only with reference to the accompanying drawings, of which:

FIG. 10 shows a schematic diagram of a first embodiment of apparatus according to the present invention;

FIG. 11 shows a schematic diagram of a second embodiment of apparatus according to the present invention;

FIG. 12 shows a schematic diagram of a third embodiment of apparatus according to the invention;

FIG. 13 shows a schematic diagram of a fourth embodiment of apparatus according to the invention;

DETAILED DESCRIPTION OF SOME EXEMPLIFYING EMBODIMENTS

Figure 1:
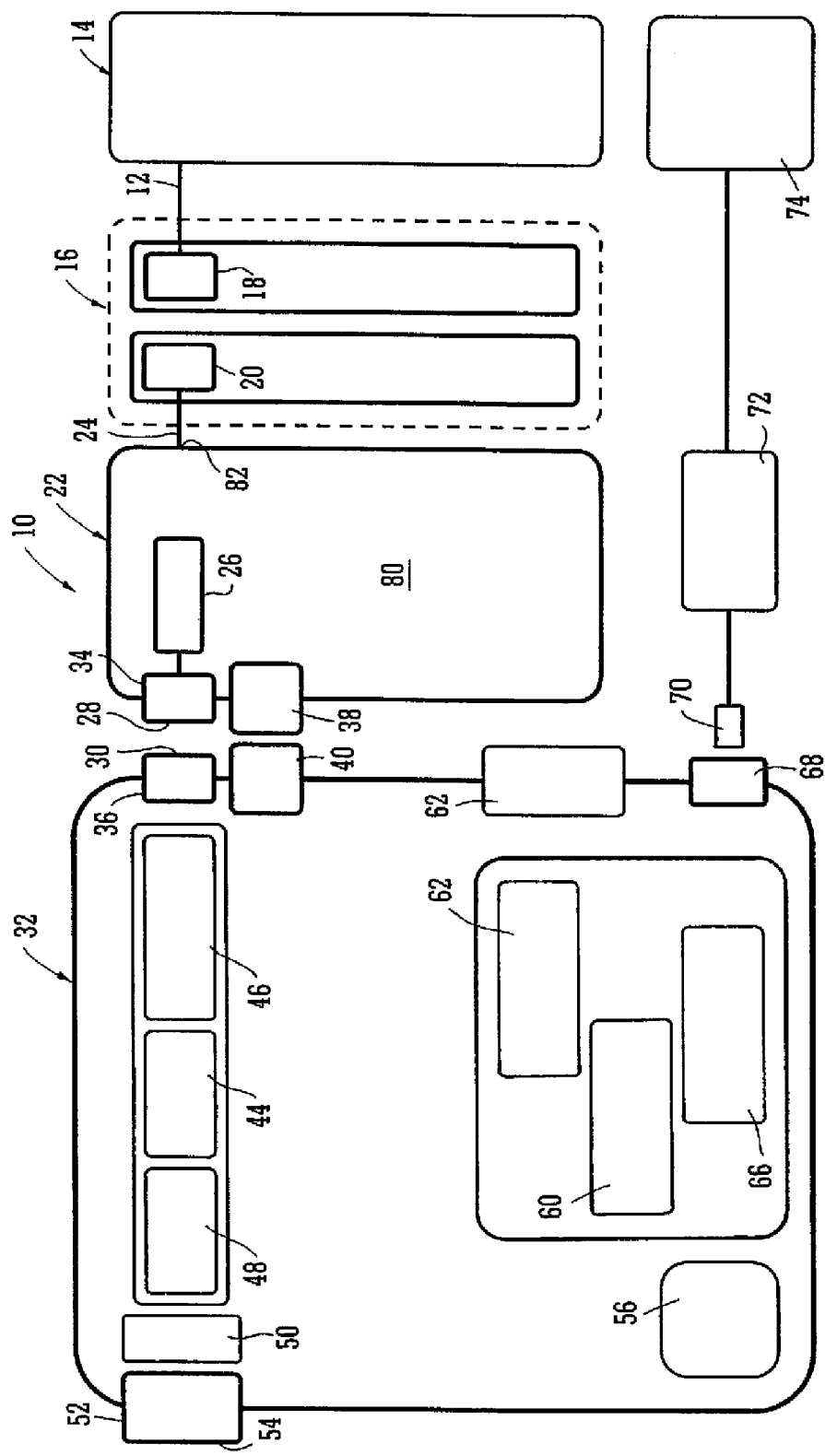
FIG. 1 shows a generalised schematic block diagram showing a general view of an apparatus and the constituent apparatus features thereof.

Referring now to FIGS. 1 to 4 of the drawings and where the same or similar features are denoted by common reference numerals.

FIG. 1 shows a generalised schematic view of an apparatus 10 of a portable topical negative pressure (TNP) system. It will be understood that embodiments of the present invention are generally applicable to use in such a TNP system. Briefly, negative pressure wound therapy assists in the closure and healing of many forms of "hard to heal" wounds by reducing tissue oedema; encouraging blood flow and granular tissue formation; removing excess exudate and may reduce bacterial load (and, therefore, infection). In addition the therapy allows for less disturbance of a wound leading to more rapid healing. The TNP system is detailed further hereinafter but in summary includes a portable body including a canister and a device with the device capable of providing an extended period of continuous therapy within at least a one year life span. The system is connected to a patient via a length of tubing with an end of the tubing operably secured to a wound dressing on the patient.

More particularly, as shown in FIG. 1, the apparatus comprises an aspiration conduit 12 operably and an outer surface thereof at one end sealingly attached to a dressing 14. The dressing 14 will not be further described here other than to say that it is formed in a known manner from well know materials to those skilled in the dressings art to create a sealed cavity over and around a wound to be treated by TNP therapy with the apparatus of the present invention. The aspiration conduit has an in-line connector 16 comprising connector portions 18, 20 intermediate its length between the dressing 14 and a waste canister 22. The aspiration conduit between the connector portion 20 and the canister 22 is denoted by a different reference numeral 24 although the fluid path through conduit portions 12 and 24 to the waste canister is continuous. The connector portions 18, 20 join conduit portions 12, 24 in a leak-free but disconnectable manner. The waste canister 22 is provided with filters 26 which prevent the escape via an exit port 28 of liquid and bacteria from the waste canister. The filters may comprise a 1 µM hydrophobic liquid filter and a 0.2 µm bacteria filter such that all liquid and bacteria is confined to an interior waste collecting volume of the waste canister 22. The exit port 28 of the waste canister 22 mates with an entry/suction port 30 of a device unit 32 by means of mutually sealing connector portions 34, 36 which engage and seal together automatically when the waste canister 22 is attached to the device unit 32, the waste canister 22 and device unit 32 being held together by catch assemblies 38, 40. The device unit 32 comprises an aspirant pump 44, an aspirant pressure monitor 46 and an aspirant flowmeter 48 operably connected together. The aspiration path takes the aspirated fluid which in the case of fluid on the exit side of exit port 28 is gaseous through a silencer system 50 and a final filter 52 having an activated charcoal matrix which ensures that no odours escape with the gas exhausted from the device 32 via an exhaust port 54. The filter 52 material also serves as noise reducing material to enhance the effect of the silencer system 50. The device 32 also contains a battery pack 56 to power the apparatus which battery pack also powers the control system 60 which controls a user interface system 62 controlled via a keypad (not shown) and the aspiration pump 44 via signals from sensors 46, 48. A power management system 66 is also provided which controls power from the battery pack 56, the recharging thereof and the power requirements of the aspirant pump 44 and other electrically operated components. An electrical connector 68 is provided to receive a power input jack 70 from a SELV power supply 72 connected to a mains supply 74 when the user of the apparatus or the apparatus itself is adjacent a convenient mains power socket.

Figure 2:
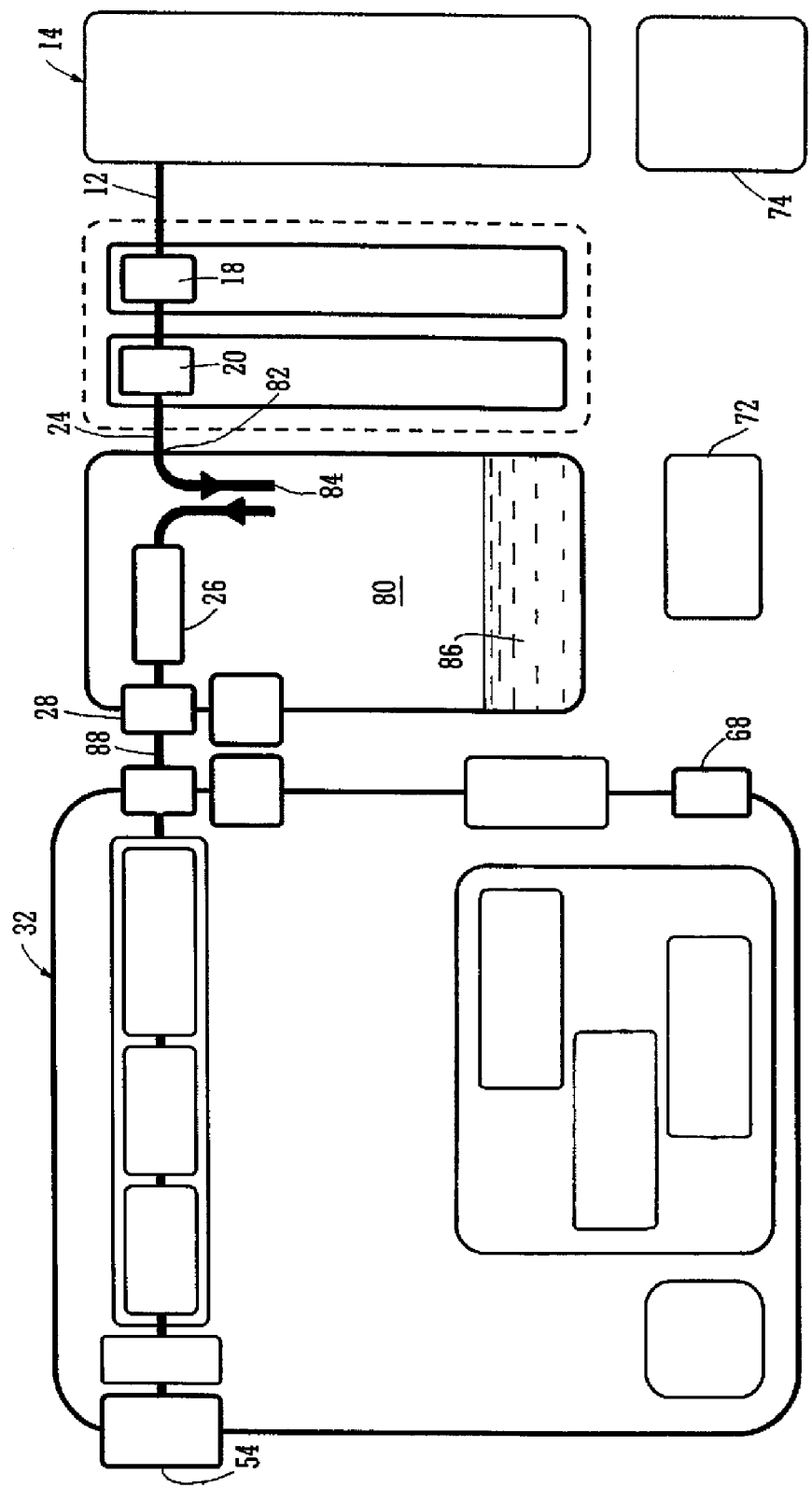
FIG. 2 shows a similar generalised schematic block diagram to FIG. 1 and showing fluid paths therein.

FIG. 2 shows a similar schematic representation to FIG. 1 but shows the fluid paths in more detail. The wound exudate is aspirated from the wound site/dressing 14 via the conduit 12, the two connector portions 18, 20 and the conduit 24 into the waste canister 22. The waste canister 22 comprises a relatively large volume 80 in the region of 500 ml into which exudate from the wound is drawn by the aspiration system at an entry port 82. The fluid 84 drawn into the canister volume 80 is a mixture of both air drawn into the dressing 14 via the semi-permeable adhesive sealing drape (not shown) and liquid 86 in the form of wound exudates. The volume 80 within the canister is also at a lowered pressure and the gaseous element 88 of the aspirated fluids is exhausted from the canister volume 80 via the filters 26 and the waste canister exhaust exit port 28 as bacteria-free gas. From the exit port 28 of the waste canister to the final exhaust port 54 the fluid is gaseous only.

Figure 3:
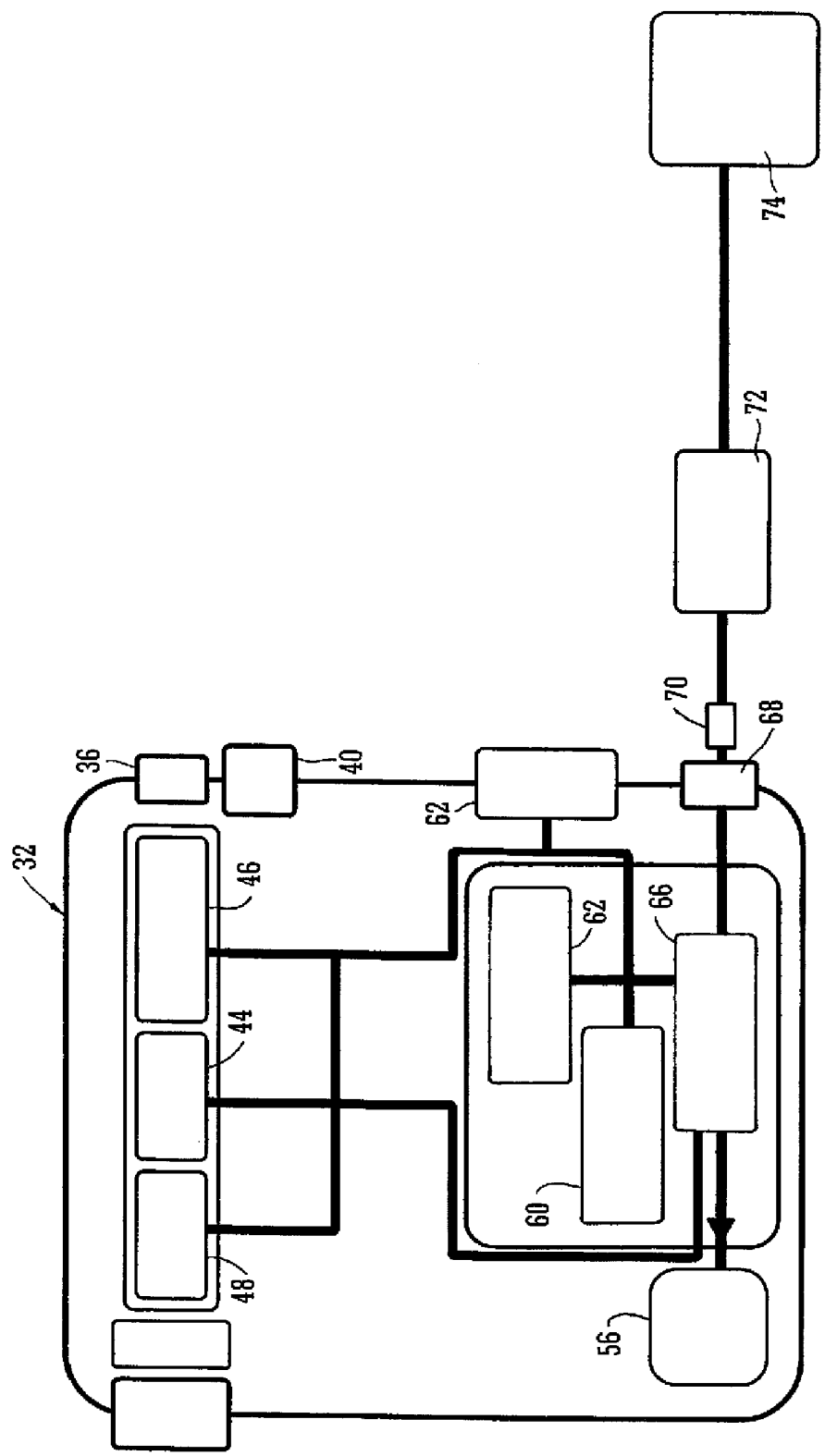
FIG. 3 shows a generalised schematic block diagram similar to FIG. 1 but of a device unit only and showing power paths for the various power consuming/producing features of the apparatus.

FIG. 3 shows a schematic diagram showing only the device portion of the apparatus and the power paths in the device of the apparatus embodying the present invention. Power is provided mainly by the battery pack 56 when the user is outside their home or workplace, for example, however, power may also be provided by an external mains 74 supplied charging unit 72 which when connected to the device 32 by the socket 68 is capable of both operating the device and recharging the battery pack 56 simultaneously. The power management system 66 is included so as to be able to control power of the TNP system. The TNP system is a rechargeable, battery powered system but is capable of being run directly from mains electricity as will be described hereinafter more fully with respect to the further figures. If disconnected from the mains the battery has enough stored charge for approximately 8 hours of use in normal conditions. It will be appreciated that batteries having other associated life times between recharge can be utilised. For example batteries providing less than 8 hours or greater than 8 hours can be used. When connected to the mains the device will run off the mains power and will simultaneously recharge the battery if depleted from portable use. The exact rate of battery recharge will depend on the load on the TNP system. For example, if the wound is very large or there is a significant leak, battery recharge will take longer than if the wound is small and well sealed.

Figure 4:
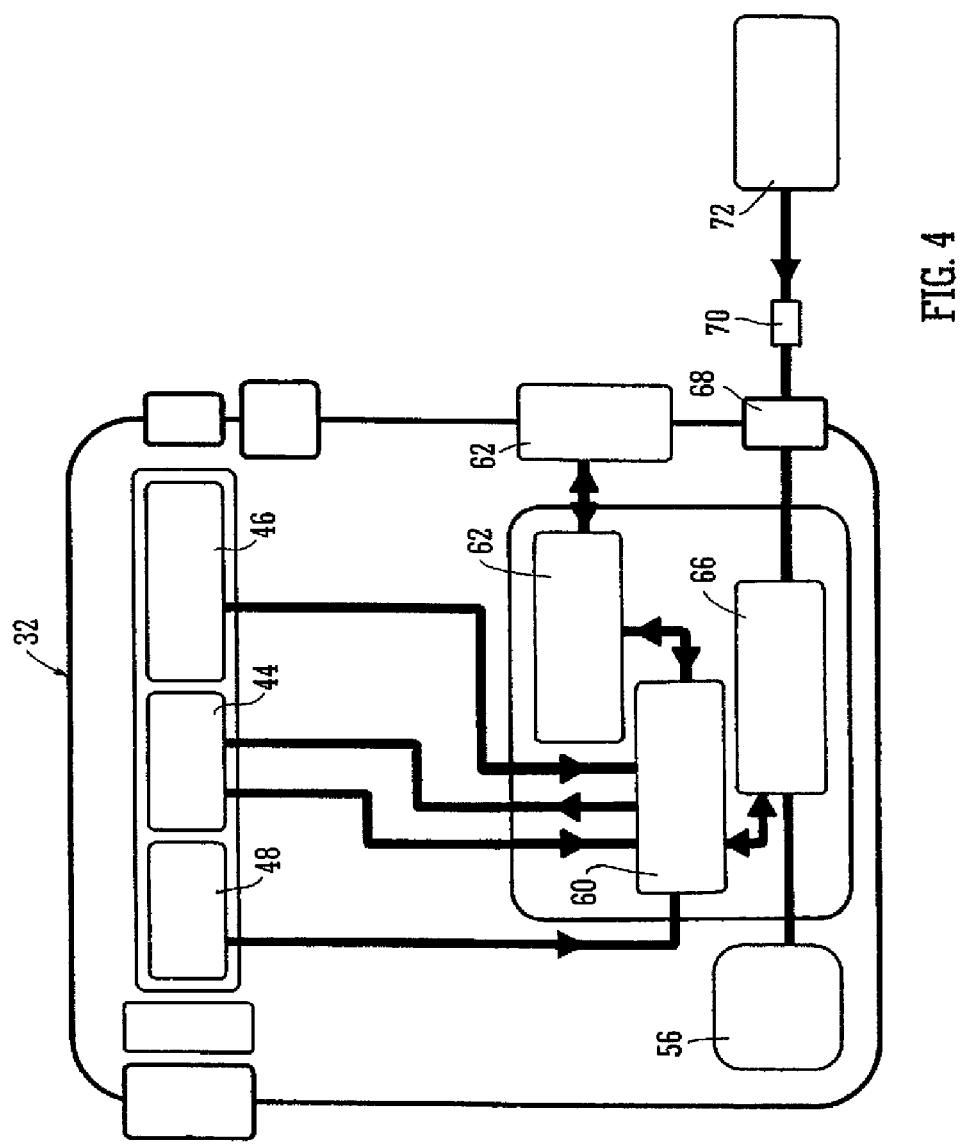
FIG. 4 shows a similar generalised schematic block diagram to FIG. 3 of the device unit and showing control system data paths for controlling the various functions and components of the apparatus.
Figure 5:
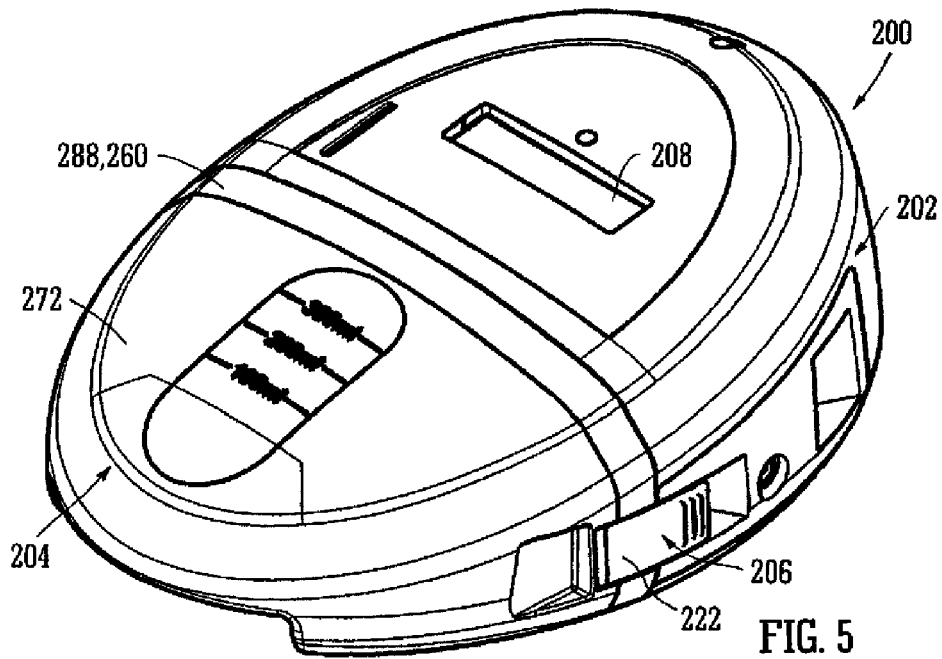
FIG. 5 shows a perspective view of an apparatus.
Figure 6:
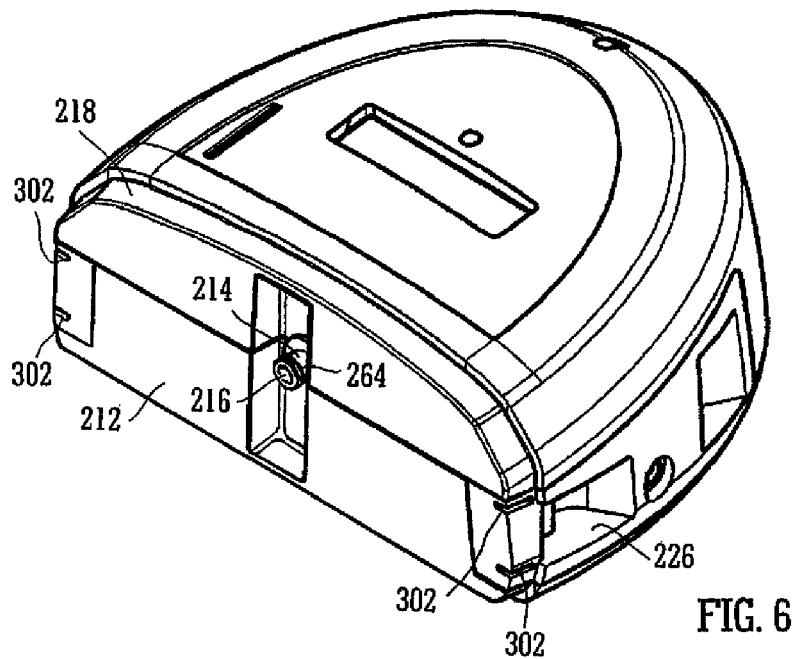
FIG. 6 shows a perspective view of an assembled device unit of the apparatus of FIG. 5.
Figure 7:
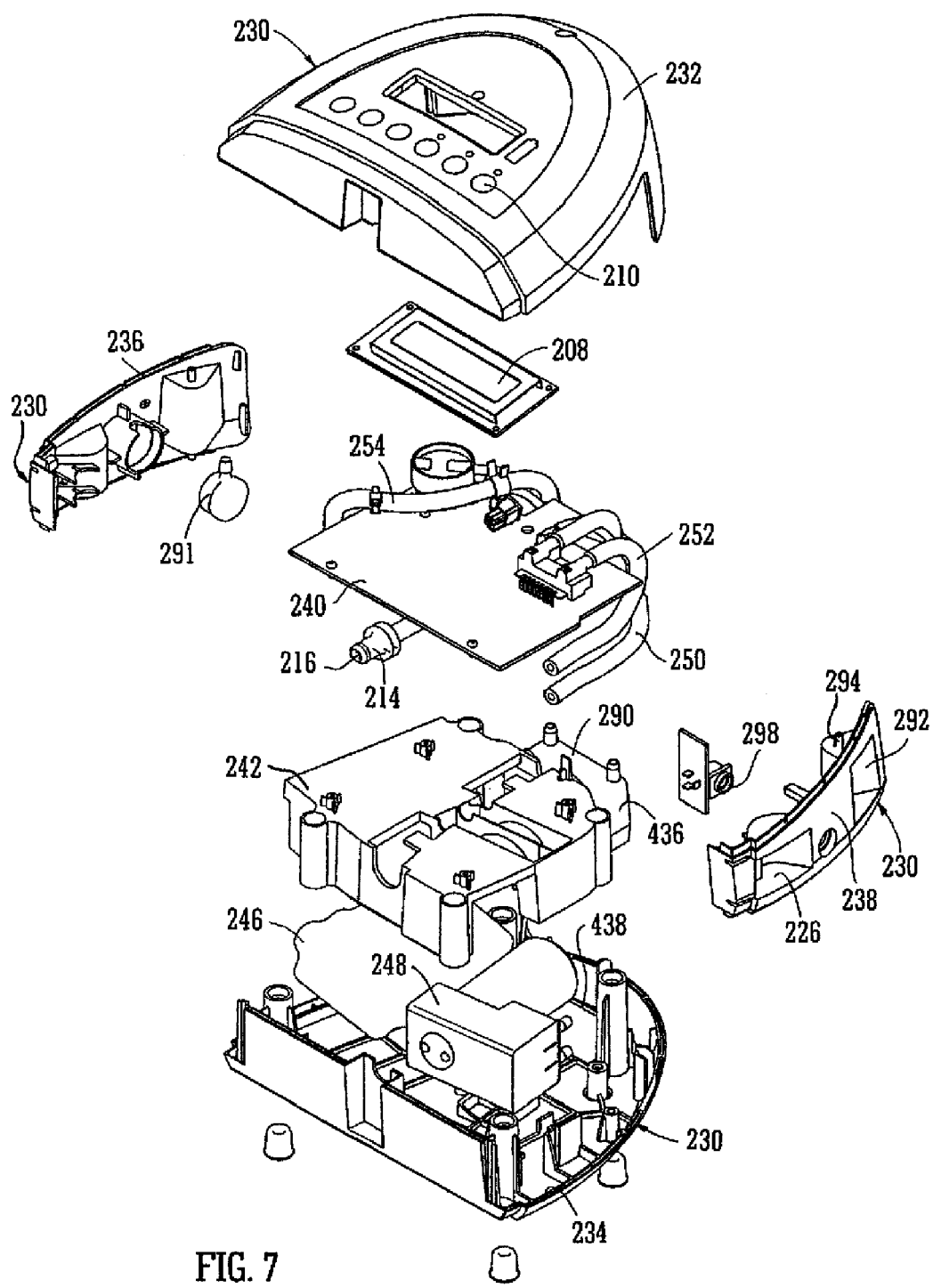
FIG. 7 shows an exploded view of the device unit of FIG. 6.

FIG. 4 shows the device 32 part of the apparatus embodying the present invention and the data paths employed in the control system for control of the aspirant pump and other features of the apparatus. A key purpose of the TNP system is to apply negative pressure wound therapy. This is accomplished via the pressure control system which includes the pump and a pump control system. The pump applies negative pressure; the pressure control system gives feedback on the pressure at the pump head to the control system; the pump control varies the pump speed based on the difference between the target pressure and the actual pressure at the pump head. In order to improve accuracy of pump speed and hence provide smoother and more accurate application of the negative pressure at a wound site, the pump is controlled by an auxiliary control system. The pump is from time to time allowed to "free-wheel" during its duty cycle by turning off the voltage applied to it. The spinning motor causes a "back electro-motive force" or BEMF to be generated. This BEMF can be monitored and can be used to provide an accurate measure of pump speed. The speed can thus be adjusted more accurately than can prior art pump systems.

According to embodiments of the present invention, actual pressure at a wound site is not measured but the difference between a measured pressure (at the pump) and the wound pressure is minimised by the use of large filters and large bore tubes wherever practical. If the pressure control measures that the pressure at the pump head is greater than a target pressure (closer to atmospheric pressure) for a period of time, the device sends an alarm and displays a message alerting the user to a potential problem such as a leak.

In addition to pressure control a separate flow control system can be provided. A flow meter may be positioned after the pump and may be used to detect when a canister is full or the tube has become blocked. If the flow falls below a certain threshold, the device sounds an alarm and displays a message alerting a user to the potential blockage or full canister.

Figure 8:
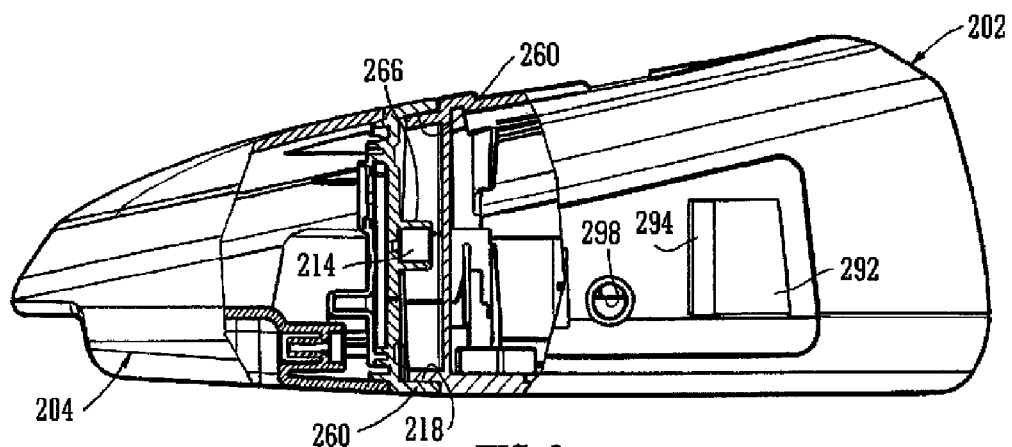
FIG. 8 shows a partially sectioned side elevation view through the interface between a waste canister and device unit of the apparatus.
Figure 9:
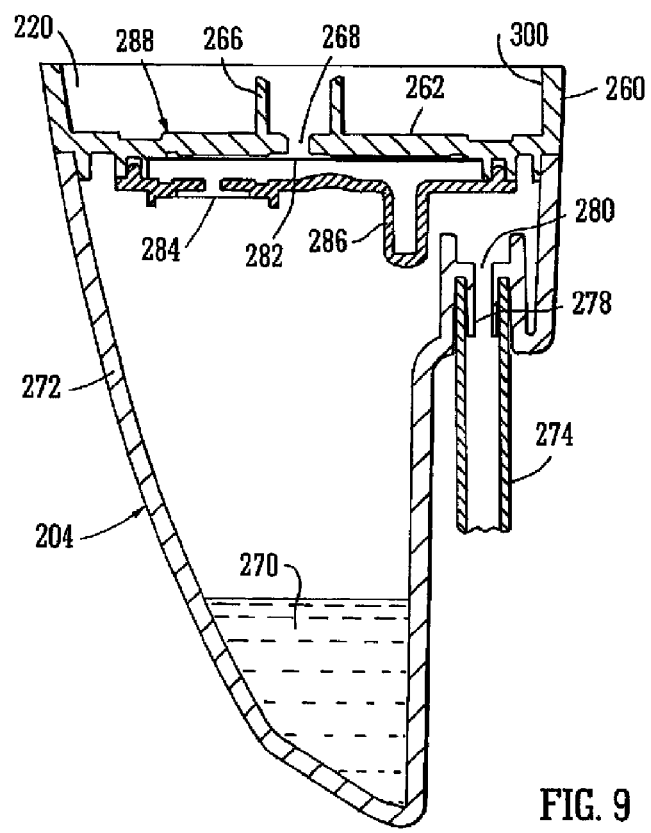
FIG. 9 shows a cross section through a waste canister of the apparatus of FIGS. 5 to 8.

Referring now to FIGS. 5 to 9 which show various views and cross sections of a preferred embodiment of apparatus 200 embodying the present invention. The preferred embodiment is of generally oval shape in plan and comprises a device unit 202 and a waste canister 204 connected together by catch arrangements 206. The device unit 202 has a liquid crystal display (LCD) 208, which gives text based feedback on the wound therapy being applied, and a membrane keypad 210, the LCD being visible through the membrane of the keypad to enable a user to adjust or set the therapy to be applied to the wound (not shown). The device has a lower, generally transverse face 212 in the centre of which is a spigot 214 which forms the suction/entry port 216 to which the aspiration means (to be described below) are connected within the device unit. The lower edge of the device unit is provided with a rebated peripheral male mating face 218 which engages with a co-operating peripheral female formation 220 on an upper edge of the waste canister 204 (see FIGS. 8 and 9). On each side of the device 202, clips 222 hinged to the canister 204 have an engaging finger (not shown) which co-operates with formations in recesses 226 in the body of the device unit. From FIG. 7 it may be seen that the casing 230 of the device unit is of largely "clamshell" construction comprising front and back mouldings 232, 234, respectively and left-hand and right-hand side inserts 236, 238. Inside the casing 230 is a central chassis 240 which is fastened to an internal moulded structural member 242 and which chassis acts as a mounting for the electrical circuitry and components and also retains the battery pack 246 and aspiration pump unit 248. Various tubing items 250, 252, 254 connect the pump unit 248 and suction/entry port 216 to a final gaseous exhaust via a filter 290. FIG. 8 shows a partially sectioned side elevation of the apparatus 200, the partial section being around the junction between the device unit 202 and the waste canister 204, a cross section of which is shown at FIG. 9. Theses views show the rebated edge 218.*of* the male formation on the device unit co-operating with the female portion 220 defined by an upstanding flange 260 around the top face 262 of the waste canister 204. When the waste canister is joined to the device unit, the spigot 214 which has an "O" ring seal 264 therearound sealingly engages with a cylindrical tube portion 266 formed around an exhaust/exit port 268 in the waste canister. The spigot 214 of the device is not rigidly fixed to the device casing but is allowed to "float" or move in its location features in the casing to permit the spigot 214 and seal 264 to move to form the best seal with the bore of the cylindrical tube portion 266 on connection of the waste canister to the device unit. The waste canister 204 in FIG. 9 is shown in an upright orientation much as it would be when worn by a user. Thus, any exudate 270 would be in the bottom of the internal volume of waste receptacle portion 272. An aspiration conduit 274 is permanently affixed to an entry port spigot 278 defining an entry port 280 to receive fluid aspirated from a wound (not shown) via the conduit 274. Filter members 282 comprising a 0.2 μm filter and 284 comprising a 1 μm filter are located by a filter retainer moulding 286 adjacent a top closure member or bulkhead 288 the filter members preventing any liquid or bacteria from being drawn out of the exhaust exit port 268 into the pump and aspiration path through to an exhaust and filter unit 290 which is connected to a casing outlet moulding at 291 via an exhaust tube (not shown) in casing side piece 236. The side pieces 236, 238 are provided with recesses 292 having support pins 294 therein to locate a carrying strap (not shown) for use by the patient. The side pieces 230 and canister 204 are also provided with features which prevent the canister and device from exhibiting a mutual "wobble" when connected together. Ribs (not shown) extending between the canister top closure member 288 and the inner face 300 of the upstanding flange 260 locate in grooves 302 in the device sidewalls when canister and device are connected. The casing 230 also houses all of the electrical equipment and control and power management features, the functioning of which was described briefly with respect to FIGS. 3 and 4 hereinabove. The side piece 238 is provided with a socket member 298 to receive a charging jack from an external mains powered battery charger (both not shown).

Referring now to FIGS. 10 to 15 and where the same or similar features are denoted by common reference numerals. In essence the same numerals notation as used in FIGS. 1 to 4 hereinabove is used for FIGS. 10 to 15 except where they differ and which will be explained as appropriate.

FIG. 10 shows a similar system to FIG. 1 comprising: a dressing 14; aspirant conduit 12, 24; waste canister 22 having filters 26 on an exit port thereof; internal tubing 400 in the device 32 linking an aspirant vacuum pump 44 and an exhaust 54 (which may or may not have a filter therein). However, in this first embodiment of apparatus according to the present invention, the flowmeter 48 of FIGS. 1 to 4 is replaced by a combination of a fluid flow restrictor 402 and pressure sensors 404, 406. The flow in the fluid flow path from the canister downstream of the filters 26 to the exhaust 54 is essentially gaseous fluid flow since liquids and bacteria are retained in the waste canister by the filters 26. The fluid flow restrictor 402 is a small aperture having a diameter in the range 0.1 to 0.5 mm in the fluid flow path intended to raise the pressure in the fluid on the upstream side of the restrictor relative to that on the downstream side under normal aspiration conditions when there is fluid flow through the system (up to the filter 26 the fluid is a mixture of gas and liquid). Pressure signals indicated by arrows 410 and 412 are communicated to the control system module 60 (see FIGS. 1-4) by the sensors 404, 406. When the pressure difference between sensors 404, 405 falls below a critical value stored in the memory of the control system 60 the control system recognises this condition as a "blockage" and/or "canister full" condition and triggers a visual and/or audible alarm (not shown). The pseudo-code for the logic sequence has the form below:

```
Check for blockage
    Get pressure sensor value f (current)
        If f(current)< min pressure needed
            Sound buzzer
            Display "Blockage/Full" error message
End check for blockage.
```

FIG. 11 shows a similar system to FIG. 10 but uses a single pressure monitor 420 which monitors directly the pressure differential between the two positions upstream and downstream of the flow restrictor 402. The control system works in the same manner being triggered by the sensor 420 signals 422 when a pressure difference below a pre-stored minimum is reached.

FIG. 12 shows a third embodiment where two pressures sensors 440, 442 are placed upstream of the pump 44 and between the pump 44 and flow restriction 402. When the canister becomes full or the aspiration conduit blocked, pressure in the tubing 400 will still be a negative pressure (below ambient atmospheric) and the pressure sensor 440 will show a negative pressure. However, due to little or no flow of aspirant fluid through the pump 44, the pressure sensor 442 will show effectively ambient atmospheric pressure which will pertain through the exhaust system to the exhaust aperture 54. Thus, if the pressure differential between sensors 440 and 442 signalled to the control system 60 is a negative differential the control system 60 will still activate the alarm. In reality the pressure differential is always likely to be negative since the pressure read by sensor 440 will be in the region of −50 to −200 mm Hg, i.e. the negative pressure being applied at the wound site/dressing 14. The pressure in sensor 442 may be in the range from 0 to 5 mm Hg. Thus, an alarm may be activated by the control system 60 when the pressure read by sensor 442 approaches ambient indicating low to zero flow through the restrictor 402.

FIG. 13 shows a fourth embodiment where the flow restrictor 402 is placed between the canister 22 and pump 44 with pressure sensors 450, 452 placed between the canister and flow restrictor and between the flow restrictor and pump, respectively. When aspirant fluid flow through the restrictor 402 falls to zero due to a full canister or blocked conduit, the two pressure sensors 450, 452 will both have the same reading albeit both reading a negative pressure as the pump is still running. Thus, equal or pressure signals less than a stored difference to the control system 60 will result in the alarm being activated.

Figure 14:
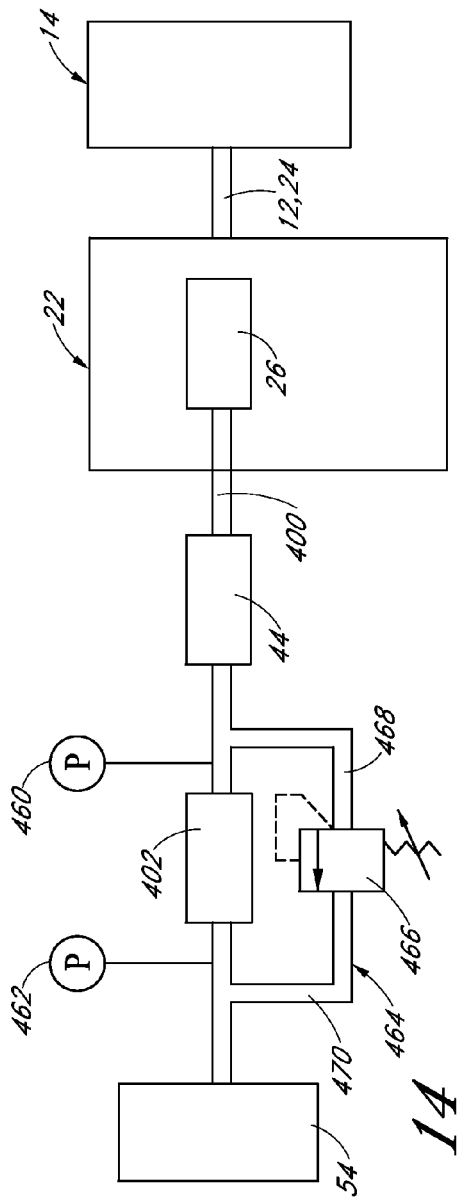
FIG. 14 shows a schematic diagram of a fifth embodiment of apparatus according to the invention.

FIG. 14 shows a schematic diagram of a fifth embodiment where a flow restrictor 402 is placed downstream of the pump 44 and which has pressure sensors 460, 462 placed either side as in FIG. 10, for example, however, in this embodiment, there is a bypass conduit 464 placed across the flow restrictor, the by-pass conduit 464 having an adjustable pressure sensitive valve 466 therein. The valve 466 may be a simple, spring loaded device able to be set to open at a desired specific pressure. Thus, when, for example, there is relatively unrestricted fluid flow through the flow system in the overall apparatus due to the canister being less than full and the aspiration conduits 12, 24 being free and unblocked, the pump will have an unnecessary burden placed upon it due to the flow restrictor 402 impeding flow and consequently the pump 44 will be operating inefficiently. Under these conditions pressure in the portion of the by-pass conduit 468 will exceed a pressure set in the valve 466 (for example +5 mm Hg) and the valve will consequently open to allow relatively unrestricted fluid flow through the valve 466 into the downstream portion 470 of the by-pass conduit 464. The valve will operate to open and close so that pressure in the by-pass conduit portion 468 is always at or slightly below the value set in the valve 466. Under the circumstances when the flow of aspirant fluid starts to deteriorate sufficiently due to the aspirant conduit 12, 24 becoming blocked or the canister approaching full, the pressure in the by-pass conduit portion 468 will fall below the set level in the valve 466 and consequently the valve 466 will then close permanently (unless a blockage of the conduits 12, 24 or filters 26 is cleared). As gaseous fluid flow rate continues to fall the pressure monitored by sensor 460 will fall and eventually approach that sensed by sensor 462 until the stored pressure differential value in the control system memory is reached which signals to the control system 60 that the alarm be activated.

Figure 15:
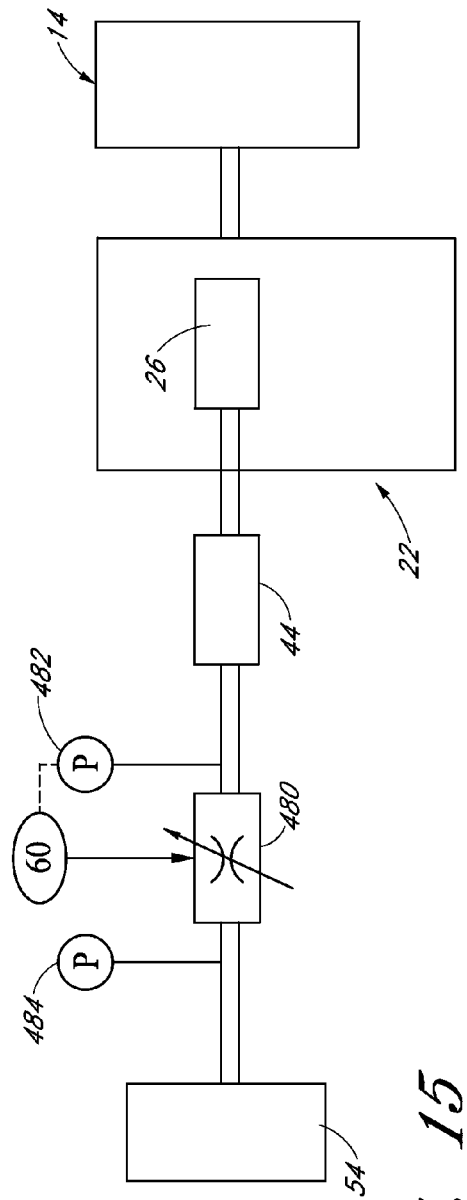
FIG. 15 which shows a schematic diagram of a sixth embodiment of apparatus according to the invention.

FIG. 15 shows a sixth embodiment where the fixed aperture fluid flow restrictor of previous embodiments is replaced by a variable area aperture flow restrictor 480. In this embodiment an objective is to reduce or minimise any undue or unnecessary burden or load on the pump 44 as with the embodiment of FIG. 15. Similarly, when there is no blockage of any kind and fluid flow is relatively high and unrestricted a small restriction places an unnecessary burden on the pump rendering it inefficient in operation. Therefore, in this embodiment, the first pressure sensor 482 downstream of the pump 44 and upstream of the variable restrictor 480 is electrically connected to the control system 60. When the pressure sensed by sensor 482 exceeds a stored value in the control system memory, for example, greater than +5 mm Hg, the control system signals the variable aperture flow restrictor 480 to increase the aperture area therein and so reduce the load or burden on the pump 44. The variable area flow restrictor 480 may be a proportional device where the aperture area is proportional to the pressure sensed at the pressure sensor 482 or may be a step device where the area is changed in predetermined increments or decrements according to the pressure sensed. As fluid flow in the apparatus falls due to a blockage or full canister the pressure sensed by sensor 482 falls to a level below that stored in the control system memory and the area of the aperture in the variable area flow restrictor is reduced to a lower, predetermined area. As gaseous fluid flow continues to fall the pressure in the first sensor 482 falls and approaches that sensed by a second sensor 484 downstream of the variable area flow restrictor 480. As in previous embodiments when fluid flow deteriorates sufficiently, signals from the two pressure sensors 482, 484 to the control system 60 eventually result in an alarm being activated.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

The invention claimed is:

1. A topical negative pressure therapy apparatus comprising:
   a vacuum pump;
   a waste canister configured to be connected to the vacuum pump, the waste canister comprising a housing defining an interior volume, the interior volume configured to collect fluid removed from a wound;
   an aspiration lumen configured to operably connect the waste canister to a wound dressing configured to enclose the wound, wherein the aspiration lumen, the waste canister, and the vacuum pump are configured to provide a fluid flow path and the vacuum pump is configured to remove fluid from the wound;
   a fluid flow restrictor positioned in the fluid flow path outside of the interior volume of the waste canister, the fluid flow restrictor comprising an entry port in fluid communication with the fluid flow path and an exit port in fluid communication with the fluid flow path, wherein at least some fluid removed from the wound is configured to flow through the flow restrictor, and wherein the fluid flow restrictor comprises a fixed-sized conduit sized to raise a pressure of fluid flow at the entry port of the fluid flow restrictor in relation to a pressure of fluid flow at the exit port of the fluid flow restrictor;
   a fluid pressure sensor configured to measure a pressure differential between the entry and exit ports of said fluid flow restrictor as at least some of the fluid removed from the wound flows through the flow restrictor; and
   a controller coupled to the fluid pressure sensor, the controller configured to activate an alarm indicating a full waste canister condition or a fluid flow path blockage condition by:
      comparing the pressure differential to a pressure difference threshold, and
      determining based on the comparison whether to activate the alarm.

2. An apparatus according to claim 1, comprising two fluid pressure sensors configured to measure the pressure differential between the entry and exit ports of the fluid flow restrictor.

3. An apparatus according to claim 1, wherein the fixed-sized conduit of the fluid flow restrictor has a diameter in the range from about 0.05 to about 1.0 mm.

4. An apparatus according to claim 1, wherein the fluid flow restrictor is positioned in the fluid flow path downstream of the vacuum pump.

5. An apparatus according to claim 1, wherein the fluid flow restrictor is positioned in the fluid flow path upstream of the vacuum pump.

6. An apparatus according to claim 1, wherein the controller is configured to activate the alarm in response to determining that the pressure differential falls below the pressure difference threshold.

7. An apparatus according to claim 6, wherein the pressure difference threshold substantially corresponds to an ambient atmospheric pressure level.

8. An apparatus according to claim 1, further comprising a bypass conduit placed across the fluid flow restrictor, the bypass conduit configured to allow flow of fluid removed from the wound to substantially bypass the fluid flow restrictor.

9. An apparatus according to claim 8, wherein the bypass conduit comprises an adjustable valve configured to:
   open when a pressure in at least a portion of the bypass conduit exceeds a flow threshold so that substantially entire flow of fluid removed from the wound is directed through the bypass conduit, and
   close when the pressure in at least the portion of the bypass conduit falls below the flow threshold so that substantially entire flow of fluid removed from the wound is directed through the fluid flow restrictor.

10. An apparatus according to claim 1, wherein the pressure difference threshold is indicative of a rate of fluid flow through the fluid flow restrictor when a blockage is present in the fluid flow path or the canister is full.

11. An apparatus according to claim 1, wherein the fixed-sized conduit of the fluid flow restrictor has a diameter in the range of about 0.1 mm and about 0.5 mm.

12. An apparatus according to claim 1, wherein the fixed-sized conduit of the fluid flow restrictor has a diameter of about 0.5 mm or less.

13. An apparatus according to claim 1, wherein the fixed-sized conduit of the fluid flow restrictor has a diameter of less than about 1.0 mm.

14. An apparatus according to claim 8, wherein the bypass conduit comprises an adjustable valve.

* * * * *

UNITED STATES PATENT AND TRADEMARK OFFICE
CERTIFICATE OF CORRECTION

PATENT NO. : 8,974,429 B2
APPLICATION NO. : 12/672055
DATED : March 10, 2015
INVENTOR(S) : Benjamin Gordon et al.

Page 1 of 1

It is certified that error appears in the above-identified patent and that said Letters Patent is hereby corrected as shown below:

In the specification

In column 3 at line 59, Change "be," to --be--.

In column 10 at line 33, Change "218." to --218--.

In column 11 at line 34 (approx.), Change "405" to --406--.

Signed and Sealed this
Twenty-fourth Day of November, 2015

Michelle K. Lee
*Director of the United States Patent and Trademark Office*